United States Patent [19]

Yoshida

[11] Patent Number: 4,507,123
[45] Date of Patent: Mar. 26, 1985

[54] MEDICAL CONTAINERS

[75] Inventor: Takao Yoshida, Fujinomiya, Japan

[73] Assignee: Terumo Kabushiki Kaisha, Tokyo, Japan

[21] Appl. No.: 426,217

[22] Filed: Sep. 28, 1982

[30] Foreign Application Priority Data

May 28, 1982 [JP] Japan .................................. 57/89864

[51] Int. Cl.³ .............................................. A61M 5/00
[52] U.S. Cl. .................................................... 604/408
[58] Field of Search ................... 604/408–410; 128/DIG. 24

[56] References Cited

U.S. PATENT DOCUMENTS

| | | | |
|---|---|---|---|
| 3,298,597 | 1/1967 | Bellamy, Jr. ......................... | 604/408 |
| 4,119,267 | 10/1978 | Kydonieus ........................... | 604/408 |
| 4,280,497 | 7/1981 | Warner et al. ....................... | 604/408 |
| 4,286,597 | 9/1981 | Gajewski et al. .................... | 604/408 |
| 4,300,559 | 11/1981 | Gajewski et al. .................... | 604/408 |
| 4,301,800 | 11/1981 | Collins ................................. | 604/408 |
| 4,337,768 | 7/1982 | Hatada et al. ....................... | 604/408 |

Primary Examiner—C. Fred Rosenbaum
Assistant Examiner—Michelle N. Lester
Attorney, Agent, or Firm—Frishauf, Holtz, Goodman & Woodward

[57] ABSTRACT

A medical container, formed by preparing two laminated sheets each having superposed, on the inner surface of an outer layer or a soft vinyl chloride resin compound composed of vinyl chloride type resin and a plasticizer, an inner layer of a soft vinyl chloride resin compound composed of vinyl chloride resin of a lower polymerization degree than the vinyl chloride resin used in the outer layer and a plasticizer, superposing the two laminated sheets with their respective inner layers adjoining each other, and sealing the common edges thereof defining a stated shape of bag by high-frequency heating.

22 Claims, 2 Drawing Figures

MEDICAL CONTAINERS

BACKGROUND OF THE INVENTION

1. Field of the Invention

This invention relates to medical containers, and more particularly to medical containers such as blood bags and transfusion bags which are provided with a sheetlike joint and made of a vinyl chloride resin compound.

2. Description of Prior Arts

Medical containers such as blood bags and transfusion bags have heretofore been produced by piling two pre-cut sheets of a vinyl chloride resin compound one on top of the other and sealing their common edges by high-frequency heating. High fabricability, physiological safety, transparency, low cost and the like are main reasons for the choice of vinyl chloride resin compound as the material. In the case of the conventional vinyl chloride resin, the sealing by high-frequency heating has entailed the disadvantage that the sealed portions of sheets tend to sustain tears or pinholes when the temperature is too high and the joined faces of sheets tend to peel when the temperature is too low.

Generally concerning sheets of synthetic resins, it has been proposed to improve the heat sealing property by using sheets of dissimilar materials widely different in thermal resistance. This method, however, has proved impracticable with soft vinyl chloride resin because this resin shows poor fusibility with other resins and loses its flexibility when exposed to the conditions of lamination. The aforementiond medical containers such as blood bags and transfusion bags normally contain medicinal solutions such as anticoagulants and liquids for transfusion. The conventional containers made of vinyl chloride resin compound have suffered these medicinal solutions to be lost by evaporation because the resin has relatively high perviousness to steam.

It is, therefore, an object of this invention to provide novel medical containers. Another object of this invention is to provide medical containers which do not sustain tears and pinholes in the sealed portions when the sealing is effected by high-frequency heating. Yet another object of this invention is to provide containers made of a vinyl chloride resin of low previousness to steam and high flexibility and used for holding medicinal solutions.

SUMMARY OF THE INVENTION

The objects described above are attained by a medical container which is produced by preparing two laminated sheets each having superposed, on the inner surface of an outer layer made of a soft vinyl chloride resin compound composed of vinyl chloride resin and a plasticizer, an inner layer made of a soft vinyl chloride resin compound composed of vinyl chloride resin of a lower polymerization degree than the vinyl chloride resin used in the outer layer and a plasticizer, superposing the two laminated sheets with their respective inner layers adjoining each other, and sealing the common edges thereof defining a stated shape of bag by high-frequency heating.

PREFERRED EMBODIMENT OF THE INVENTION

Figure 1:
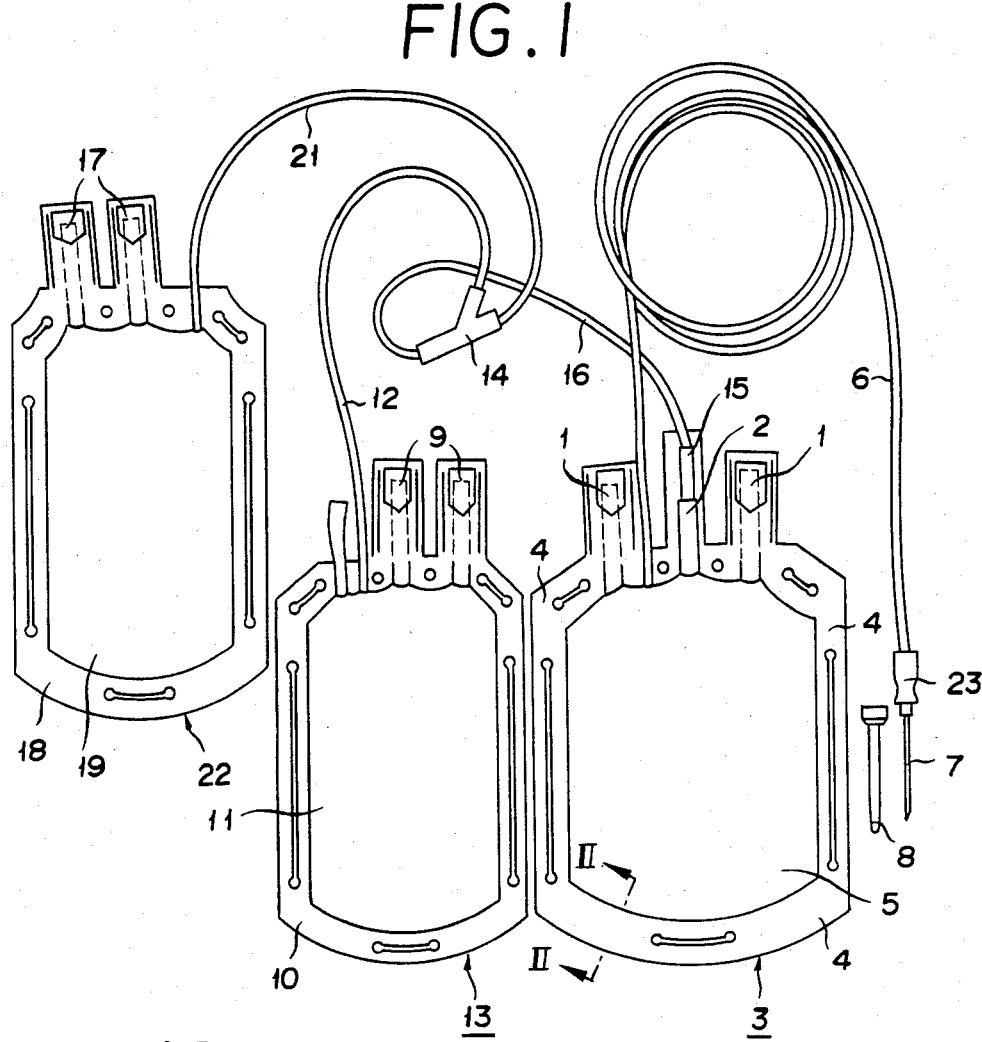
FIG. 1 is a front view illustrating a typical medical container according to this invention.

Polyvinyl choride, a copolymer formed of vinyl chloride as a main component and other copolymerizable monomer, or polyvinylidene chloride may be usable as the vinyl chloride resin which forms the outer layer of the medical container of the present invention. The polymer is required to have an average degree of polymerization in the range of 1000 to 3000, preferably 2000 to 3000. Examples of the comonomer usable with vinyl chloride in the aforementioned copolymer are vinylidene chloride, lower olefins such as ethylene and propylene, vinyl acetate, vinyl bromide, vinyl fluoride, styrene, vinyl toluene, vinyl pyridine, acrylic acid, alkyl acrylates such as methyl acrylate, ethyl acrylate, isopropyl acrylate and butyl acrylate, methacrylic acid, alkyl methacrylates such as methyl methacrylate and ethyl methacrylate, acrylonitrile and methacrylonitrile. The aforementioned vinyl chloride type resin may incorporate therein styrene-acrylonitrile copolymer, styrene-methyl methacrylate copolymer or other similar polymer.

Examples of the plasticizer used for enhancing the flexibility of the vinyl chloride resin are phthalic esters such as dibutyl phthalate, dihexyl phthalate, di-2-ethylhexyl phthalate, di-n-octyl phthalate, di-isooctyl phthalate, diheptyl phthalate, didecyl phthalate, diisodecyl phthalate, octyldecyl phthalate and butylbenzyl phthalate; trimellitic esters such as tributyl trimellitate and trioctyl trimellitate; aliphatic polybasic acid esters such as dioctyl adipate, dioctyl azelate and dioctyl sebacate; phosphoric esters such as tricresyl phosphate, trixylenyl phosphate, monooctyldiphenyl phosphate, monobutyldixylenyl phosphate and trioctyl phosphate; citric esters such as tributylacetyl citrate, trioctylacetyl citrate and tributyl citrate and epoxidized vegetable oils such as epoxidized soybean oil and epoxidized linseed oil. Such a plasticizer is generally incorporated in a proportion of 30 to 80 phr, preferably 40 to 70 phr.

In the aforementioned combination of vinyl chloride resin and a plasticizer, a metal soap of such a metal as barium, zinc or calcium with such an organic acid as stearic acid, lauric acid, ricinolic acid, naphthenic acid or 2-ethylhexoic acid, an organic tin such as dibutyl tin laurate or dibutyl tin dimaleate may be incorporated, when required, in conjunction with a slidant and other additives.

Examples of the vinyl chloride resin which forms the inner layer are polyvinyl chloride, vinyl chloride copolymers and polyvinylidene chloride similarly to the vinyl chloride resin for the outer layer. This vinyl chloride resin may incorporate therein other polymer. This vinyl chloride resin is required to have a lower average degree of polymerization than the resin used in the outer layer, generally in the range of 700 to 1500, preferably 1000 to 1500. The monomers cited above as usable for the outer layer are similarly usable for the inner layer. The plasticizers cited above as usable for the outer layer are similar by usable for the inner layer. The amount of such a plasticizer to be incorporated is desired to be equal to or greater than that used for the outer layer, generally in the range of 40 to 80 phr, preferably 50 to 70 phr. The kinds of stabilizers and their amounts for addition are the same as for the outer layer.

When desired, the stabilizers may be used in conjunction with a lubricant and other additives.

The soft vinyl chloride resin compound to form the inner layer is desired to incorporate therein 0 to 7% by weight, preferably 1 to 4% by weight, based on the plasticizer of silicone oil as emulsified with part of the plasticizer, for the purpose of precluding possible exudation of the plasticizer from the layer, preventing the layer from undergoing the phenomenon of blocking while the container is sterilized with high-pressure steam, and protecting the surface of the layer against deposition of blood platelets. Examples of the silicon oil include polymethylphenyl siloxane, polydimethyl siloxane, polydiphenyl siloxane, polydimethylmethylphenyl siloxane, polydimethyldiphenyl siloxane and polymethylhydrodiene siloxane. Although the outer layer has less necessity for the incorporation of silicone oil than the inner layer, it may naturally incorporate silicone oil.

Various methods are conceivable for adoption in the manufacture of a laminate sheet having dissimilar degrees of polymerization in the outer and inner layers. For example, the laminate sheet may be produced by extruding the resin composition for one of the layers in a molten state through a die, spreading the extruded molten resin in the shape of a sheet on the surface of the other layer, and joining them under pressure. Alternatively, it may be produced by simultaneously extruding the two resin compositions for the layers through separate dies and immediately superposing the extruded layers under pressure. Otherwise, it may be obtained by preparing the two layers as separate sheets and superposing then under application of heat and pressure. The thickness of the outer layer is desired to be in the range of 0.05 to 0.3 mm, preferably 0.1 to 0.3 mm and that of the inner layer to be in the range of 0.1 to 0.4 mm, preferably 0.1 to 0.3 mm.

In this invention, the vinyl chloride resin to form the inner layer is required to have a lower degree of polymerization than the resin to form the outer layer. The reason for the lower degree of polymerization of the resin for the outer layer is that since generally a resin of a lower degree of polymerization has higher flexibility and higher flowability at melting point than a resin of a higher degree of polymerization, the sealing by high-frequency heating to be effected at the temperature meeting the melting conditions of the inner layer will suffice for fusing only the adjoining inner layers without substantially deforming the outer layer and, consequently, the otherwise possible occurrence of tears and pinholes in the sealed portion owing to the harsh conditions of sealing can be precluded.

An effective heat seal between two laminated sheets each formed of an inner and an outer layer using vinyl chloride type resins dissimilar in average degree of polymerization can be obtained by adjoining their respective layers of a lower degree of polymerization and subjecting their pertinent portions to high-frequency heating.

Now, one preferred embodiment of the present invention will be described below with reference to the accompanying drawings. FIG. 1 represents a blood bag. A blood collection bag 3 which is made of soft polyvinyl chloride and provided with a discharge outlet 1 fitted with a plurality of peel tabs and connecting outlets 2 has its periphery 4 heat-sealed by high-frequency heating as will be described afterward and also has connected thereto a blood collection tube 6 made of soft vinyl chloride resin compound and communicating with the inner cavity 5 of the blood collection bag. The blood collection bag contains in the inner cavity 5 thereof an ACD-A solution (containing 2.20 g of sodium citrate, 0.80 g citric acid and 2.20 g of grape sugar in 100 ml of aqueous solution thereof, for example) or a CPD solution (containing 206 mg of citric acid, 1.66 g of sodium citrate, 140 mg of disodium phosphate and 1.46 g of dextrose in 100 ml of an aquoeus solution thereof, for example) as an anticoagulant. The aforementioned blood collection tube 6 is provided at the tip thereof with a blood collection needle 7. A cap 8 is fitted on this blood collection needle 7.

The blood bag may have other auxiliary bags connected thereto in addition to the aforementioned blood collection bag 3. A first auxiliary bag 13 which is made of soft vinyl chloride resin compound and provided with discharge outlets 9 each fitted with a peel tab and which has its periphery 10 similarly heat-sealed by high-frequency heating and has connected thereto a connection tube made of soft vinyl chloride resin compound and communicating with an inner cavity 11 is connected via a manifold 14 to a connection tube 16 which is connected to the connecting outlet 2 of the blood collection bag 3 through the medium of a connection needle 15 provided at the leading end of the connection tube 16. A second auxiliary bag 22 which is provided with discharge outlets 17 each fitted with a peel tab and which has its periphery 18 similarly selaed and has connected thereto a connection tube 21 of made soft vinyl chloride resin compound and communicating with an inner cavity 19 thereof is connected through the medium of the connection tube 21 of its own to the connection tubes 12, 16 via the manifold 14.

Figure 2:
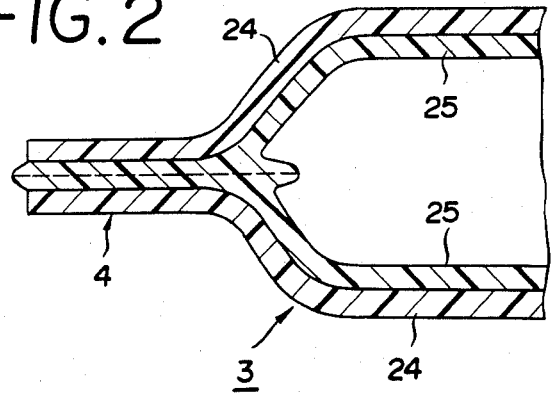
FIG. 2 is an enlarged sectional view taken along the line II—II of the diagram of FIG. 1.

The blood collection bag 3 and the auxiliary bags 13, 22 are each formed, for example, by preparing two laminated sheets each having superposed, on the inner surface of an outer layer 24 made of a soft vinyl chloride resin compound composed of vinyl chloride resin and a plasticizer, an inner layer 25 made of a soft vinyl chloride resin compound composed of vinyl chloride resin of a lower polymerization degree than the vinyl chloride resin used in the outer layer and a plasticizer, superposing the two laminated sheets with their respective inner layers 25, 25 adjoining, and sealing the common edges 4 thereof defining the shape of the bag in question by high-frequency heating as illustrated in FIG. 2. In the edges 4, the high-frequency heating fuses the inner layers 25, 25 intimately to form a seal and hardly affects the outer layers 24, 24.

The blood bag has been described above as a typical embodiment of this invention. Of course, the description applies, with necessary modifications, to transfusion bags and other forms of medical containers contemplated by this invention. It should be noted that in FIG. 2, all the layers of the sheets are illustrated with exaggerated thicknesses.

Now, the present invention will be described more specifically below with reference to working examples.

EXAMPLE 1

TABLE 1

| Components for resin composition | Inner layer (phr) | Outer layer (phr) |
|---|---|---|
| | $\bar{p}$: 1000 | $\bar{P}$: 2000 |
| Polyvinyl chloride | 100 | 100 |
| Di-2-ethylhexyl phahalate | 55 | 55 |
| Epoxidized soybean oil | 3 | 3 |
| Stabilizer | 0.05 | 0.3 |

TABLE 1-continued

| Components for resin composition | Inner layer (phr) | Outer layer (phr) |
| --- | --- | --- |
| Slidant | 0.1 | 0.3 |

A laminated sheet was prepared by superposing an inner layer 25 (0.2 mm in thickness) of the composition shown in Table 1 on an outer layer 24 (0.2 mm in thickness) of the composition shown in the same table. Two portions each of the shape and size of a blood bag 3 desired to be made were cut from the laminated sheet. These two portions were superposed with their respective inner layers 25, 25 adjoining each other, and their common edges 4 were heat-sealed by high-frequency heating to produce the blood bag 3. In this each, the temperature difference of flow value between the inner layer 25 and the outer layer 24 was 15° to 20° C. In the sealed portion, the thickness of the inner layer 25 was changed and that of the outer layers 24 remained substantially intact as illustrated in FIG. 2.

The sealed portion of the blood bag was examined to take count of pinholes. The results were as shown in Table 1.

Separately, a sheet 0.4 mm in thickness was prepared by using solely the resin composition of the outer layer. A blood bag was produced from this sheet by repeating the procedure described above. This blood bag was examined to take count of pinholes. The results were as shown in Table 2.

TABLE 2

| One-layer sheet (0.4 mm) | 5/1000 bags |
| --- | --- |
| Two-layer sheet (0.2 mm each of inner and outer layers) | 0/1000 bags |

EXAMPLE 2

A laminated sheet was prepared by superposing an inner layer 25 (0.175 mm in thickness) of the composition shown in Table 1 on an outer layer 24 (0.175 mm in thickness) of the composition shown in the same table. Two portions each of the shape and size of a blood bag 3 desired to be produced were cut from the laminated sheet. Then, the two portions were superposed with their respective inner layers 25, 25 adjoining each other, and the common edges 4 were heat-sealed by high-frequency heating at 46 MHz to complete the blood bag 3.

The blood bag thus produced was tested for seal strength with a tensile tester under the conditions of 10 mm of width and 180° of peeling direction. The results were as shown in Table 3.

TABLE 3

| Thickness of sealed portion (in mm) | Sealing time (in sec) | |
| --- | --- | --- |
| | 1.8 | 3.0 |
| | Seal strength (in kg) | |
| 0.30 | 4.3 | 4.1 |
| 0.32 | 4.5 | 4.6 |
| 0.36 | 4.5 | 4.4 |
| 0.38 | 4.5 | 4.5 |
| 0.40 | 4.3 | 4.5 |
| 0.42 | 4.3 | 4.3 |
| 0.44 | 3.9 | 3.9 |

EXAMPLE 3

A blood bag was produced by following the procedure of Example 2. It was tested for seal strength at varying points of the sealed portion. The result were as shown in Table 4.

TABLE 5

| Thickness of sealed portion (in mm) | Sealing time (in sec) | |
| --- | --- | --- |
| | 1.8 | 3.0 |
| | Seal strength (in kg) | |
| 0.30 | 3.1 | 3.2 |
| 0.34 | 4.1 | 3.4 |
| 0.38 | 4.2 | 4.1 |
| 0.42 | 4.3 | 4.0 |
| 0.46 | 4.4 | 4.5 |
| 0.50 | 4.6 | 4.4 |

EXAMPLE 4

The procedure of Example 2 was repeated, except that the thickness of the inner layer and that of the outer layer were each changed to 0.2 mm. The results were as shown in Table 5.

TABLE 4

| Point of measurement | Seal strength (in kg) |
| --- | --- |
| Top | 4.4 |
| Righthand side | 4.6 |
| Lefthand side | 4.6 |
| Bottom | 4.5 |

As described above, the medical container of the present invention is produced by preparing two laminated sheets each having superposed, on the inner surface of an outer layer of a soft vinyl chloride resin compound composed of vinyl chloride resin and a plasticizer, an inner layer of a soft vinyl chloride resin composition composed of vinyl chloride resin of a lower polymerization degree than the vinyl chloride resin used in the outer layer and a plasticizer, superposing the two laminated sheets with their respective inner layers adjoining each other, and sealing the common edges thereof defining a stated shape of bag by high-frequency heating. Since the inner layer has higher flexibility and higher flowability at melting point than the outer layer having a higher average polymerization degree, the sealing by high-frequency heating to be effected at the temperature meeting the melting conditions of the inner layer will suffice for fusing only the adjoining inner layers without substantially deforming the outer layer and, consequently, the otherwise possible occurrence of tears and pinholes in the sealed portion owing to the harsh conditions of sealing can be precluded. Since the heat seal is formed between the adjoining inner layers of a resin of heat seal is formed between the adjoining low polymerization degree, the blood container enjoys high flexibility and shows low previousness to steam. Thus, the products by this invention are particularly useful as medical containers such as blood bags and transfusion bags which serve to contain medicinal solutions.

What is climed is:

1. A medical container for housing a liquid, comprising:
 means defining a liquid receiving chamber, said means comprising two sheets, each of said sheets having an inner layer and an outer layer superposed on each other and defining a common peripheral edge portion which extends around said chamber, said common peripheral edge portion being sealed together such that the inner layer of one of said sheets adjoins and is sealed to the inner layer of the other of said sheets in said common peripheral edge portion, said outer layer comprising a soft vinyl chloride resin compound comprising a first vinyl chloride resin and a plasticizer; and said inner layer comprising a soft vinyl chloride resin compound comprising a second vinyl chloride resin and a plasticizer, said second vinyl chloride resin having a lower degree of polymerization than said first vinyl chloride resin.

2. The medical container according to claim 1, wherein the thickness of the outer layer is in the range of 0.05 to 0.3 mm and the thickness of the inner layer is in the range of 0.1 to 0.4 mm.

3. The medical container according to claim 1, wherein the amount of the plasticizer in each of the vinyl chloride resin compounds of the inner and outer layers is in the range of 30 to 80 phr.

4. The medical container according to claim 3, wherein the soft vinyl chloride resin compound of the inner layer further comprises 0 to 7% by weight, based on the weight of the plasticizer, of a silicone oil as emulsified with part of the plasticizer.

5. The medical container according to claim 3, wherein the amount of the plasticizer in each of the vinyl chloride resin compounds of the inner and outer layers is in the range of 40 to 70 phr.

6. The medical container according to claim 1, wherein the medical container is a container holding therein a medicinal solution.

7. The medical container according to claim 6, wherein the container holding therein a medicinal solution is a blood bag.

8. The medical container according to claim 6, wherein the container holding therein a medicinal solution is a transfusion bag.

9. The medical container according to claim 2, wherein the thickness of the outer layer is in the range of 0.1 to 3.0 mm and the thickness of the inner layer is in the range of 0.1 to 0.3 mm.

10. The medical container according to claim 2, wherein the amount of the plasticizer in each of the vinyl chloride resin compounds of the inner and outer layers is in the range of 30 to 80 phr.

11. The medical container according to claim 2, wherein the soft vinyl chloride resin compound of the inner layer further comprises 0 to 7% by weight, based on the weight of the plasticizer, of a silicone oil as emulsified with part of the plasticizer.

12. The medical container according to claim 10, wherein the soft vinyl chloride resin compound of the inner layer further comprises 0 to 7% by weight, based on the weight of the plasticizer, of a silicone oil as emulsified with part of the plasticizer.

13. The medical container according to claim 2, wherein the medical container is a container holding therein a medicinal solution.

14. The medical container according to claim 10, wherein the medical container is a container holding therein a medicinal solution.

15. The medical container according to claim 1, wherein the common peripheral edge portion is sealed together by high-frequency heating.

16. A medical container for housing a liquid, comprising:

means defining a liquid receiving chamber, said means comprising two sheets, each of said sheets having an inner layer and an outer layer superposed on each other and defining a common peripheral edge portion which extends around said chamber, said common peripheral edge portion being sealed together such that the inner layer of one of said sheets adjoins and is sealed to the inner layer of the other of said sheets in said common peripheral edge portion, said outer layer comprising a soft vinyl chloride resin compound comprising a first vinyl chloride resin having an average degree of polymerization of from 1000 to 3000 and a plasticizer; and said inner layer comprising a soft vinyl chloride resin compound comprising a second vinyl chloride resin having an average degree of polymerization of from 700 to 1500 and a plasticizer, said second vinyl chloride resin having a lower degree of polymerization than said first vinyl chloride resin.

17. The medical container according to claim 16, wherein the average degree of polymerization of the first vinyl chloride resin is in the range of 2000 to 3000 and the average degree of polymerization if the second vinyl chloride resin is in the range of 1000 to 1500.

18. The medical container according to claim 16, wherein the thickness of the outer layer is in the range of 0.05 to 0.3 mm and the thickness of the inner layer is in the range of 0.1 to 0.4 mm.

19. The medical container according to claim 16, wherein the amount of the plasticizer in each of the vinyl chloride resin compounds of the inner and outer layers is in the range of 30 to 80 phr.

20. The medical container according to claim 16, wherein the soft vinyl chloride resin compound of the inner layer further comprises 0 to 7% by weight, based on the weight of the plasticizer, of a silicone oil as emulsified with part of the plasticizer.

21. The medical container according to claim 16, wherein the medical container is a container holding therein a medicinal solution.

22. The medical container according to claim 16, wherein the common peripheral edge portion is sealed together by high-frequency heating.

* * * * *

UNITED STATES PATENT AND TRADEMARK OFFICE
CERTIFICATE OF CORRECTION

PATENT NO. : 4,507,123           PAGE 1 OF 2.

DATED : March 26, 1985

INVENTOR(S) : Takao YOSHIDA

It is certified that error appears in the above-identified patent and that said Letters Patent is hereby corrected as shown below:

Column 1, line 46, change "previousness" to --perviousness--;

Column 2, line 63, change "similar by usable" to --similarly usable;

Column 3, line 63, change "discharge outlet" to --discharge outlets--;

Column 3, line 65, change "outlets 2" to --outlet 2--;

Column 4, line 8, change "aquoeus" to --aqueous--;

Column 4, line 28, change "selaed" to --sealed--;

Column 4, line 29, change "of made" to --made of--;

Column 6, line 1, change "result" to --results--;

UNITED STATES PATENT AND TRADEMARK OFFICE
CERTIFICATE OF CORRECTION

PATENT NO. : 4,507,123           PAGE 2 OF 2.
DATED      : March 26, 1985
INVENTOR(S): Takao YOSHIDA It is certified that error appears in the above-identified patent and that said Letters Patent is hereby corrected as shown below:

Column 6, TABLES 4 and 5 have been inverted, TABLE 5
should be part of EXAMPLE 4 and positioned
after the first paragraph thereof; and
TABLE 4 should be part of EXAMPLE 3 and
positioned after the first paragraph thereof;

Column 6, line 54, change "previousness" to --perviousness--.

Signed and Sealed this

Nineteenth Day of August 1986

[SEAL]

Attest:

DONALD J. QUIGG

Attesting Officer        Commissioner of Patents and Trademarks